United States Patent [19]

Saito et al.

[11] Patent Number: 4,985,581

[45] Date of Patent: Jan. 15, 1991

[54] CATALYST AND PROCESS FOR PRODUCING AROMATIC NITRILES

[75] Inventors: Masao Saito, Tokyo; Kengo Tsukahara, Niigata; Noriko Takahashi, Niigata; Yuzi Onda, Niigata, all of Japan

[73] Assignee: Mitsubishi Gas Chemical Co., Inc., Tokyo, Japan

[21] Appl. No.: 336,475

[22] Filed: Apr. 12, 1989

[30] Foreign Application Priority Data

Apr. 26, 1988 [JP] Japan ................................ 63-101401

[51] Int. Cl.$^5$ ............................................ C07C 253/28
[52] U.S. Cl. ......................................................... 558/327
[58] Field of Search ........................................... 558/327

[56] References Cited

U.S. PATENT DOCUMENTS

| | | | |
|---|---|---|---|
| 3,462,476 | 8/1969 | O'Donnell et al. | 558/327 |
| 3,772,212 | 11/1973 | Saito et al. | 558/327 X |
| 3,870,743 | 3/1975 | Ibing et al. | 558/327 |
| 3,959,339 | 5/1976 | Saito et al. | 558/327 |

FOREIGN PATENT DOCUMENTS

| | | | |
|---|---|---|---|
| 2123836 | 12/1971 | Fed. Rep. of Germany | 558/227 |
| 45-19051 | 11/1967 | Japan | 558/327 |
| 45-19284 | 1/1968 | Japan | 558/327 |
| 49-45860 | 12/1974 | Japan . | |
| 1351523 | 5/1974 | United Kingdom . | |

*Primary Examiner*—Joseph Paul Brust
*Attorney, Agent, or Firm*—Armstrong, Nikaido, Marmelstein, Kubovick & Murray

[57] ABSTRACT

The present invention relates to a catalyst which comprises a vanadium oxide, a chromium oxide, a molybdenum oxide and a boron oxide supported on a silica carrier. This catalyst is suitable for use in the production of aromatic nitriles from alkyl-substituted aromatic compound by the catalytic reaction of a gas mixture containing an alkyl-substituted aromatic compound, ammonia and oxygen or a gas containing molecular oxygen over a catalyst. The present invention further relates to a process for producing the aromatic nitriles using said catalyst.

6 Claims, No Drawings

CATALYST AND PROCESS FOR PRODUCING AROMATIC NITRILES

BACKGROUND OF THE INVENTION

This invention relates to a catalyst suitable for use in producing aromatic nitriles by catalytic reaction of a gas mixture containing an alkyl-substituted aromatic compound, ammonia, and oxygen or a gas containing molecular oxygen over such catalyst and a process for producing aromatic nitriles using the catalyst.

DESCRIPTION OF THE PRIOR ART

Aromatic nitriles are intermediates important in organic chemical industry. For example, phthalonitrile is used as a starting material for producing xylylenediamine useful as synthetic resins, agricultural agents, and curing agents for diisocyanate or epoxy resin.

Hitherto, various processes have been proposed for producing aromatic nitriles by reacting an alkyl-substituted aromatic compound, ammonia and oxygen and Japanese Patent Publication No. 45-19284 discloses the superior performances of ternary catalyst composed of vanadium, chromium and boron. Further, G.B. Patent 1351523 discloses superiority of the above ternary catalyst which comprises a vanadium oxide, a chromium oxide and a boron oxide at an atomic ratio of 1:(0.5–2.0):(0.1–1.2) supported in an amount of 30–60 % by weight on a silica carrier.

Vapor phase ammoxidation reactions of alkylsubstituted aromatic compounds generate a large amount of heat of reaction. Therefore, control of reaction temperature is very difficult and fluidized bed type reactor is especially effective for the reaction. The invention of G.B. Patent 135123 which uses silica as a carrier is an improvement of the invention of Japanese Patent Publication No. 45-19284, and the catalyst of the former is used in fluidized bed reactors and exhibits excellent performances. However, these catalysts of the prior art decrease in selectivity to the corresponding aromatic nitriles with time when used for a long time.

SUMMARY OF THE INVENTION

The inventor has been intensively researched to prevent the reduction of selectivity with time. It has been found that this can be much improved by using a four-component catalyst which a molybdenum oxide is further added to the ternary catalyst comprising a vanadium oxide, a chromium oxide and boron oxide supported on silica.

Thus, the present invention provides a catalyst suitable for use in the ammoxidation of alkyl-substituted aromatic compounds to aromatic nitriles which comprises a vanadium oxide, a chromium oxide, a molybdenum oxide and a boron oxide supported on a silica carrier.

The present invention also provides a process for producing an aromatic nitrile which comprises subjecting a gas mixture containing an alkyl-substituted aromatic compound, ammonia and oxygen or a gas containing molecular oxygen to pass over a catalyst which comprises a vanadium oxide, a chromium oxide, a molybdenum oxide and a boron oxide supported on a silica carrier.

DETAILED DESCRIPTION OF THE INVENTION

The atomic ratio of vanadium:chromium:molybdenum:boron which are catalyst components of the present invention is preferably 1:(0.5–2.0):(0.01–1.2):(0.01–1.2).

As mentioned above, since the reaction of the present invention involves vigorous generation of heat, it is advantageous to carry out the reaction in a fluidized bed or a moving bed for removal of heat of reaction to prevent partial heating, although the characteristics of the catalyst can be exhibited and the excellent performances can be maintained even if the reaction is carried out in a fixed bed.

A vanadium oxide, a chromium oxide, a molybdenum oxide and a boron oxide may be used as raw materials for the catalyst. Alternatively various compounds, which are readily converted to the corresponding oxides by suitable treatment such as heating when the catalyst is prepared, may be used. These compounds include, for example, ammonium metavanadate, vanadyl sulfate and vanadium salts of organic acids such as oxalic acid and tartaric acid etc., as the vanadium raw materials; chromic acid, chromium nitrate, chromium hydroxide, ammonium chromate, ammonium bichromate and chromium salts of organic acids such as oxalic acid and tartaric acid etc. as chromium raw materials; ammonium molybdate, ammonium paramolybdate, molybdic acid, molybdenum chloride and molybdenum salts of organic acids such as oxalic acid and tartaric acid as molybdenum raw materials; boric acid and ammonium borate as boron raw materials.

As the silica which supports these catalyst components, for example, silica gel, colloidal silica and anhydrous silica which are disclosed in "Kagaku Binran (Handbook of Chemistry), Section of Applied Chemistry I", pages 256–258 (published from Maruzen Co. in 1986). Total percentage of the catalyst component oxides in the catalyst is 20–80% by weight, preferably 30–60 % by weight (the oxides being expressed as $V_2O_5$, $CR_2O_3$, $MoO_3$ and $B_2O_3$, respectively).

The present catalyst can be prepared by known methods. For example, aqueous ammonium molybdate solution and aqueous boric acid solution are added to a solution of vanadium oxalate and chromium oxalate and then a silica sol is added thereto to obtain a slurry mixture. In this case, if necessary, a dissolving aid for boric acid is used. The dissolving aid for boric acid includes polyhydric alcohols, α-monooxycarboxylic acids, and dioxycarboxylic acids.

In the case of a fluidized bed catalyst, the resulting mixture is spray dried and, if necessary, is further dried at 110–150° C. and then calcined. In the case of a fixed bed catalyst, the mixture is evaporated to dryness and then is calcined. Calcination is carried out at 400–700° C., preferably 450–650° C. for a few hours or more while passing air. If prior to this calcination a preliminary calcination is carried out at 200–400° C., more favorable results can be obtained.

The alkyl-substituted aromatic compounds used as a starting material in the present invention include, for example, toluene, ethylbenzene, polymethylbenzene (such as xylene, mesitylene, cymene, and durene), diethylbenzene and methylnaphthalene.

A suitable concentration of the alkyl-substituted aromatic compound in the gas mixture is 0.5–5 vol % when air is used as the oxygen source.

The amount of ammonia used may be at least the theoretical amount (1 mol of ammonia per 1 mol of alkyl group). The higher molar ratio of ammonia/aromatic compound in the gas mixture is advantageous for improving yield of nitrile from the aromatic compound, but in view of the necessity to recover unreacted ammonia, amount of ammonia is the theoretical amount or more, preferably about 2-10 times as much as the theoretical amount.

Usually, air is used as oxygen source, and nitrogen, carbon dioxide or steam can be used as an inert diluent. Amount of oxygen to be fed is at least 1.5 times as much as the theoretical amount and preferably 2-50 times as much as the theoretical amount.

Temperature of the reaction can be in a wide range of 300–500° C., but preferably 330–470° C. When the temperature is lower than 300° C, conversion of the raw material aromatic compound is low and when higher than 500° C., production of carbon dioxide and hydrogen cyanide is increased, resulting in reduction in the yield of nitrile. Reaction temperature for obtaining the maximum yield of nitrile depends on the kind of aromatic compound, concentration of raw materials, contact time and calcination conditions for catalyst. So it is preferred to optionally select the reaction temperature within the above range depending on the conditions.

Contact time of the gas mixture with the catalyst may be varied over a wide range but is preferably 0.5–30 seconds.

The reaction of the present invention is usually carried out under atmospheric pressure, but can be carried out under an elevated pressure or a reduced pressure.

Collection of reaction product can be effected by any suitable methods, for example, by cooling to a temperature enough to precipitate the product or by washing the reaction product gas with water or other suitable solvent.

According to the process of the present invention which comprises carrying out the catalyst reaction of a gas mixture containing an alkyl-substituted aromatic compound, ammonia and oxygen or a gas containing molecular oxygen using a catalyst comprising a vanadium oxide, a chromium oxide, a molybdenum oxide and a boron oxide supported on a silica carrier thereby to produce aromatic nitriles, reduction with time of selectivity to the corresponding aromatic nitriles is very small and stable performance of the catalyst can be obtained for a long period of time as shown by the following examples.

DESCRIPTION OF THE PREFERRED EMBODIMENTS

The present invention will be explained in more detail by the following examples and comparative examples.

Comparative Example 1

Preparation of catalyst 500 ml of water was added to 247 g of vanadium pentoxide, $V_2O_5$, followed by heating to 80–90° C. Then, 514 g of oxalic acid, $(COOH)_2 2H_2O$ was gradually added with well stirring to obtain a vanadyl oxalate solution. Separately, 400 ml of water was added to 1029 g of oxalic acid, followed by heating to 50–60° C. Then a solution of 271 g of chromic anhydride $CrO_3$ in 200 ml of water was gradually added to the oxalic acid solution with well stirring to obtain a chromium oxalate solution.

The resulting chromium oxalate solution was mixed drop-wise with the resulting vanadyl oxalate solution at 50–60° C. to prepare a vanadium-chromium solution, to which 1667 g of a 30 wt % aqueous silica sol was further added.

To this slurry solution was added 84 g of boric acid $H_3BO_3$, then this slurry was well mixed and concentrated until amount of the liquid reached about 3570 g.

This catalyst solution was spray dried with an inlet gas temperature of 250° C. and an outlet gas temperature of 130° C. The thus spray dried catalyst was dried in a drier of 130° C. for 12 hours. Then, the catalyst was preliminary calcined at 400° C. for 0.5 hour and thereafter calcined at 550° C. for 8 hours while passing air. This catalyst had an atomic ratio V:Cr:B of 1:1:0.5 and an oxide concentration of 50 wt %.

Test for Catalyst Performance

A 40 ml of the resulting catalyst was packed in a reactor having an inner diameter of 23 mm which was heated in a molten salt bath, a preheated gas mixture consisting of 3.0 mol % of m-xylene, 21.0 mol % of ammonia and 76.0 mol % of air was contacted with the catalyst at an SV of 750 $Hr^{-1}$ and at 420° C. which gives the maximum yield of isophthalonitrile. The yield of isophthalonitrile and m-tolunitrile were 81.2 mol % and 2.7 mol % based on m-xylene respectively. Selectively of the catalyst for isophthalonitrile to the reacted m-xylene was 82.2 mol %.

By the above method, the reaction was continued for 6 months with suitably changing the reaction temperature to the temperature at which the maximum yield of isophthalonitrile is obtained. The yield of isophthalonitrile and m-tolunitrile were 75.2 mol % and 2.2 mol % based on the m-xylene. Selectivity of the catalyst for isophthalonitrile to the reacted m-xylene was 76.1 mol %.

EXAMPLE 1

Preparation of catalyst

A 500 ml of water was added to 242 g of vanadium pentoxide, $V_2O_5$, followed by heating to 80–90° C. Then, 503 g of oxalic acid, $(COOH)_2 2H_2O$ was gradually added with well stirring to obtain a vanadyl oxalate solution. Separately, 400 ml of water was added to 1016 g of oxalic acid, followed by heating to 50–60° C. Then a solution of 266 g of chromic anhydride $CrO_3$ in 200 ml of water was added to the oxalate solution with well stirring to obtain a chromium oxalate solution.

The resulting chromium oxalate solution was mixed with the resulting vanadyl oxalate solution to prepare a vanadium-chromium solution. To this solution were added drop-wise a solution of 47 g of ammonium paramolybdate $(NH_4)_6Mo_7O_{24}4H_2O$ in 300 ml of water and furthermore, 1667 g of a 30 wt % aqueous silica sol.

To this slurry solution was added 33 g of boric acid $H_3BO_3$, then this slurry was well mixed and concentrated until amount of the liquid reached about 3800 g.

This catalyst solution was spray dried with an inlet gas temperature of 250° C. and an outlet gas temperature of 130° C. The thus spray dried catalyst was dried in a drier of 130° C. for 12 hours. Then, the catalyst was preliminary calcined at 400° C. for 0.5 hour and thereafter calcined at 550° C. for 8 hours while passing air. This catalyst had an atomic ratio V:Cr:Mo:B of 1:1:0.1:0.2 and an oxide concentration of 50 wt %.

Test for catalyst performance

In the same manner as in Comparative Example 1, the resulting catalyst was examined on activity and change of performance with time.

A gas mixture consisting of 3.0 mol % of m-xylene, 21.0 mol % of ammonia and 76.0 mol % of air was fluid contacted with the catalyst at an SV of 750 $Hr^{-1}$ and at 400° C. which is a temperature to give the maximum yield of isophthalonitrile. The yield of isophthalonitrile and m-tolunitrile were 82.7 mol % and 1.3 mol % based on the m-xylene respectively. Selectivity of the catalyst for isophthalonitrile to the reacted m-xylene was 83.5 mol %.

By the above method, the reaction was continued for 6 months with suitably changing the reaction temperature to the temperature at which the maximum yield of isophthalonitrile is obtained. The yield of isophthalonitrile and m-tolunitrile were 82.5 mol % and 1.4 mol % based on the m-xylene respectively. Selectivity of the catalyst for isophthalonitrile to the reacted m-xylene was 83.3 mol %.

EXAMPLE 2

A catalyst having an atomic ratio of V:Cr:Mo:B=1:1:0.3:0.5 was prepared in the same manner as in Example 1 and activity and change of performance with time of this catalyst were examined.

A gas mixture consisting of 3.0 mol % of m-xylene, 21.0 % of ammonia and 76.0 % of air was contacted with this catalyst at an SV of 750 $Hr^{-1}$ and at 420° C. which is a temperature to give the maximum yield of isophthalonitrile. The yield of isophthalonitrile and m-tolunitrile were 79.8 mol % and 2.2 mol % based on m-xylene, respectively. Selectivity of the catalyst for isophthalonitrile to the reacted m-xylene was 80.5 mol %.

By the above method, the reaction was continued for 6 months with suitably changing the reaction temperature to the temperature at which the maximum yield of isophthalonitrile is obtained under the same conditions. The yield of isophthalonitrile and m-tolunitrile were 79.8 mol % and 2.3 mol % based on the m-xylene respectively. Selectivity of the catalyst for isophthalonitrile to the reacted m-xylene was 80.4 mol %.

EXAMPLE 3

A catalyst prepared in Example 1 was tested on activity and examined on change of performance with time in the same manner as in Example 1 except that p-xylene was used in place of m-xylene.

A gas mixture consisting of 3.1 mol % of p-xylene, 19.9 mol % of ammonia and 77.0 mol % of air was contacted with this catalyst at an SV of 800 $Hr^{-1}$ and at 400° C. which is a temperature to give the maximum yield of the phthalonitrile. The yield of terephthalonitrile and p-nitrile were 83.5 mol % and 2.5 mol % based on p-xylene, respectively. Selectivity of the catalyst for terephthalonitrile to the reacted p-xylene was 84.0 mol %.

By the above method the reaction was continued for 6 months with suitably changing the reaction temperature to the temperature at which the maximum yield of terephthalonitrile is obtained under the same conditions. The yield of terephthalonitrile and p-nitrile were 83.1 mol % and 2.3 mol % based on the p-xylene respectively. Selectivity of the catalyst for terephthalonitrile to the reacted p-xylene was 83.9 mol %.

EXAMPLE 4

The catalyst prepared in Example 1 was tested on activity and examined on change of performance with time in the same manner as in Example 1 except that toluene was used in place of m-xylene.

A gas mixture consisting of 5.1 % of toluene, 25.0 % of ammonia and 69.9 % of air was contacted with this catalyst at an SV of 840 $Hr^{-1}$ and at 410° C. which is a temperature to give the maximum yield of benzonitrile. The yield of benzonitrile was 83.3 mol % based on toluene. Selectivity of the catalyst for benzonitrile to the reacted toluene was 84.3 mol %.

By the above method, the reaction was continued for 6 months with suitably changing the reaction temperature to the temperature at which the maximum yield of benzonitrile is obtained under the same conditions. The yield of benzonitrile was 83.0 mol % based on the toluene. Selectivity of the catalyst for benzonitrile to the reacted toluene was 83.8 mol %.

What is claimed is:

1. A process for producing an aromatic nitrile comprising subjecting a gas mixture containing 0.5–5 % by volume of an alkyl-substituted aromatic compound selected from the group consisting of toluene, ethylbenzene, xylene, mesitylene, cymene, durene, diethylbenzene or methylnaphthalene, ammonia and oxygen or a gas containing molecular oxygen, to a catalytic reaction, at a reaction temperature of 300–500° C. for a contact time of 0.5–30 seconds, wherein the catalyst consists essentially of vanadium oxide, chromium oxide, molybdenum oxide and boron oxide in an atomic ratio of V:Cr:Mo:B of 1:0.5–2.0:0.01–1.2:0.01–1.2 and is supported 20–80 % by weight on a silica carrier.

2. A process according to claim 1 wherein the gas mixture contains ammonia in an amount not less than the theoretical amount.

3. A process according to claim 1 wherein the gas containing molecular oxygen is air.

4. A process according to claim 1 wherein the amount of oxygen present in the gas mixture is at least 1.5 times the theoretical amount.

5. A process according to claim 1 wherein the gas mixture containing an alkyl-substituted aromatic compound, ammonia and oxygen or a gas containing molecular oxygen is subjected to catalytic reaction with the catalyst in fluidized state.

6. A process according to claim 3 wherein the gas mixture contains 0.5–5 % by volume of the alkyl-substituted aromatic compound.

* * * * *